Figure 4G:
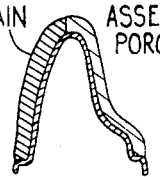
Figure 4H:
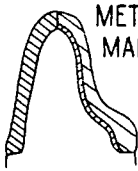
Figure 4I:
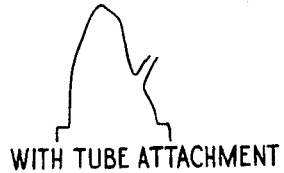
Figure 4J:
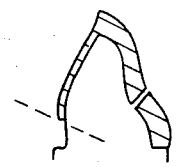
Figure 4K:
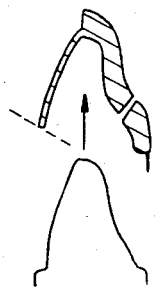
Figure 4L:
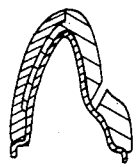
Figure 4M:
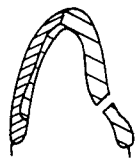
Figure 5A:
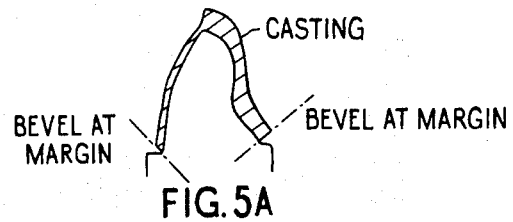
Figure 5B:
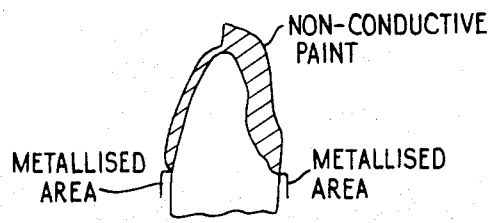

United States Patent [19]

Rogers

[11] 3,997,637
[45] Dec. 14, 1976

[54] METHOD OF MAKING TOOTH RECONSTRUCTIONS SUCH AS INLAYS AND CROWNS

[76] Inventor: Olbert William Rogers, 70 Gymea Bay Road, Gymea, New South Wales, Australia

[22] Filed: Apr. 23, 1975

[21] Appl. No.: 570,740

[30] Foreign Application Priority Data

Apr. 29, 1974 Australia ............................ 7387/74
Dec. 31, 1974 Australia ............................ 150/74

[52] U.S. Cl. .................................. 264/19; 204/20; 204/30; 264/22; 264/56; 264/129; 264/221
[51] Int. Cl.² ..................... A61C 13/8; A61C 5/10
[58] Field of Search ................ 264/16, 17, 22, 19, 264/219, 221, 222, 226, 227, 265, 317, 238, 332, 18, 56, 129; 32/2, 12, 13, 8; 204/20, 30

[56] References Cited

UNITED STATES PATENTS

| | | | |
|---|---|---|---|
| 2,118,934 | 5/1938 | Madzar | 32/12 |
| 2,317,008 | 4/1943 | Werner | 264/321 |
| 3,052,982 | 9/1962 | Weinstein et al. | 264/19 |
| 3,487,544 | 1/1970 | Weissman | 32/12 |
| 3,585,723 | 6/1971 | Simor | 32/12 |
| 3,723,585 | 3/1973 | Nussbaum | 264/219 |

OTHER PUBLICATIONS

Anon., Technique of Fusing Porcelain to Gold, Julius Aderer, Inc., N.Y., (1939), pp. 2–15 relied on.

Primary Examiner—Willard E. Hoag
Attorney, Agent, or Firm—Hill, Gross, Simpson, Van Santen, Steadman, Chiara & Simpson

[57] ABSTRACT

Method of making artificial tooth inlays and crowns by electrolytically depositing a metal, preferably gold, matrix on a preformed model and subsequently building up porcelain on the matrix. The matrix may then be removed prior to cementing the inlay or crown to the patient's tooth; or alternatively the inlay or crown may be cemented to the patient's tooth together with the matrix.

5 Claims, 43 Drawing Figures

FREE MARGIN OF SOFT GOLD
AVAILABLE FOR ADAPTATION

MATRIX LEFT IN SITU - PORCELAIN
JACKET CROWN PLACED ON TOOTH

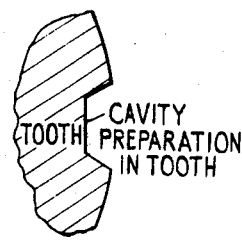

FIG.1A
CAVITY PREPARATION IN TOOTH

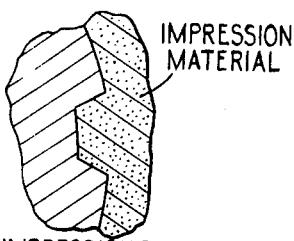

FIG.1B
IMPRESSION TAKEN OF CAVITY PREPARATION

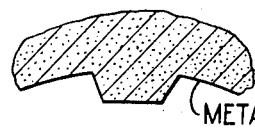

FIG.1C
IMPRESSION REMOVED AND SURFACE METALLISED TO MAKE ELECTRICALLY CONDUCTIVE

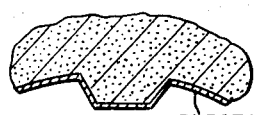

FIG.1D
ELECTROFORMED GOLD MATRIX PLACED IN ELECTROLYTE AND MATRIX ELECTRO-DEPOSITED

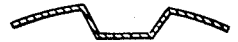

FIG.1E
GOLD MATRIX REMOVED FROM IMPRESSION MATERIAL

FIG.1F
PORCELAIN FUSED IN GOLD MATRIX

FIG.1G
GOLD REMOVED BY PLACING IN AQUA REGIA

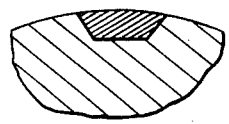

FIG.1H
PORCELAIN INLAY CEMENTED INTO TOOTH

FIG.2A
ELECTROFORMED GOLD MATRIX
ARTIFICIAL STONE MODEL

FIG.2B
ELECTROFORMED GOLD MATRIX
MATRIX REMOVED FROM STONE MODEL

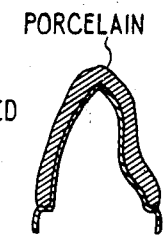

FIG.2C
PORCELAIN
PORCELAIN DEPOSITED ON TO MATRIX

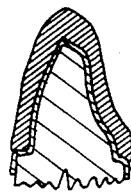

FIG.2D
MATRIX REMOVED BY AQUA REGIA AND PORCELAIN JACKET CROWN PLACED ON TOOTH

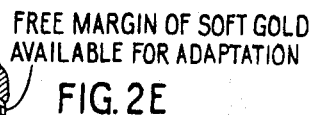

FIG.2E
FREE MARGIN OF SOFT GOLD AVAILABLE FOR ADAPTATION
MATRIX LEFT IN SITU-PORCELAIN JACKET CROWN PLACED ON TOOTH

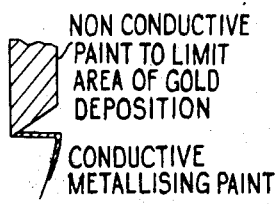
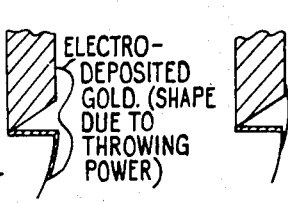
FIG. 5C    FIG. 5D    FIG. 5E    FIG. 5F
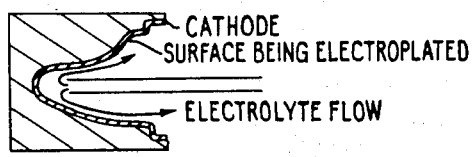
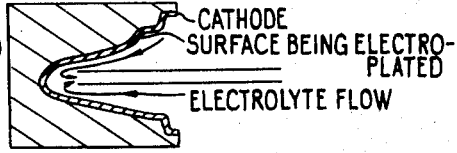
FIG. 6A      FIG. 6B

PORCELAIN — MATRICES I & II ASSEMBLED AND PORCELAIN FIXED

MATRIX I REMOVED SHOWING NO METAL AT THE PORCELAIN-GINGIVAL MARGIN TO CAUSE DISCOLOURATION

WITH TUBE ATTACHMENT

CASTING
BEVEL AT MARGIN — BEVEL AT MARGIN

NON-CONDUCTIVE PAINT
METALLISED AREA — METALLISED AREA

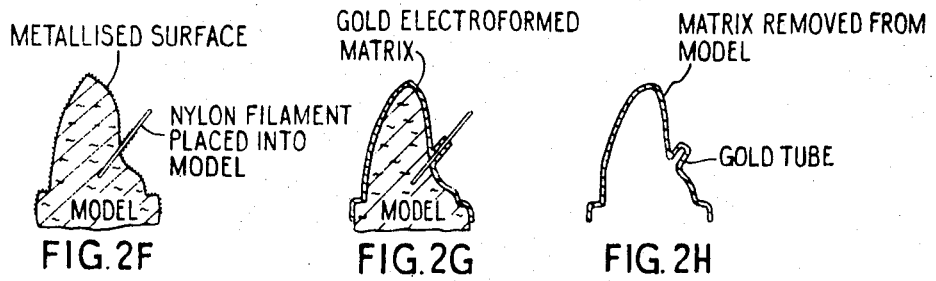
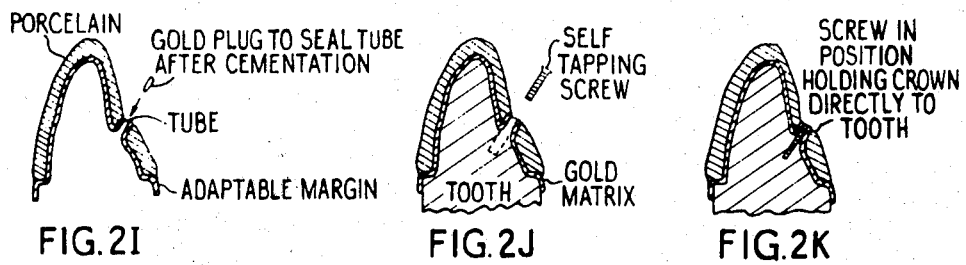
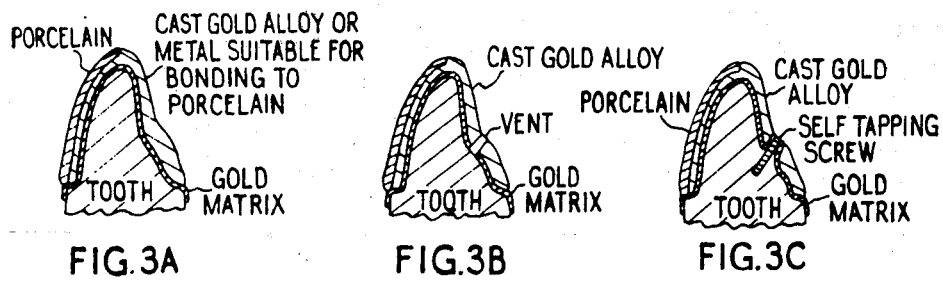
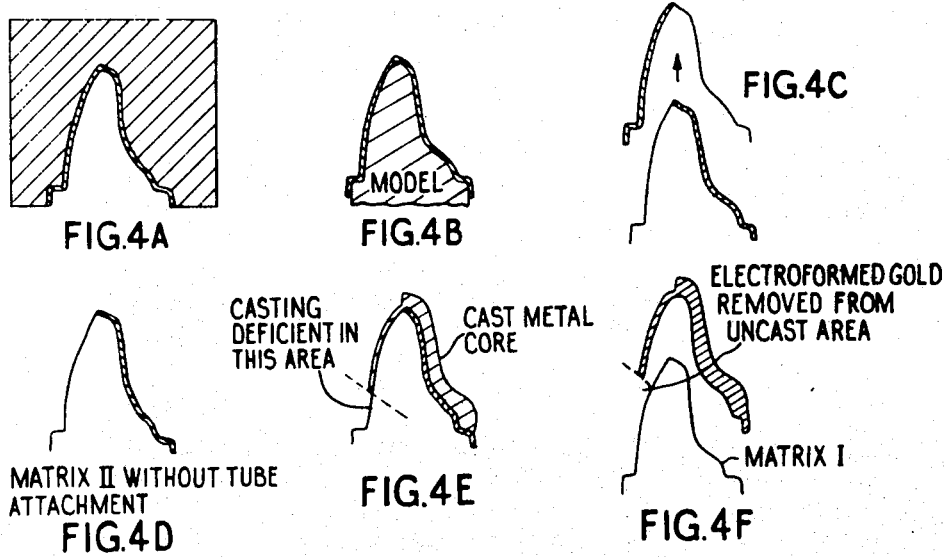

METHOD OF MAKING TOOTH RECONSTRUCTIONS SUCH AS INLAYS AND CROWNS

This invention relates to the construction of artificial teeth, that is to say, complete artificial teeth or portions thereof, such as tooth crowns or insertions.

It is common practice to construct or crown teeth with metal and/or porcelain. Porcelain has the advantage of being aesthetically more acceptable while metal, commonly, but not necessarily gold or gold alloy, is stronger or at least less brittle.

One conventional way of constructing an artificial tooth or crown involves forming a model of a patient's tooth, forming a matrix conforming to the shape of such tooth from e.g. platinum foil by burnishing the foil on to the model of such tooth, and thereafter building up and firing porcelain on the foil matrix. Thereafter, the foil is removed from the matrix and the matrix is cemented over the original tooth in the mouth of the patient. Alternatively, a matrix is cast in a metal, e.g. gold alloy, chromium/cobalt or nickel/chromium, and porcelain built up thereon for aesthetic purposes only.

This conventional method suffers from various disadvantages, more especially in that the technique leads to a series of cumulative minor errors ultimately leading to a poor fit of the artificial tooth in the patient's mouth, more especially, at the gingival areas. These errors arise from a variety of reasons including discrepancies in the original foil matrix, discrepancies between porcelain and metal in the case of composite structures, and shrinkage of the porcelain on firing which can also distort the matrix. In addition the poor fit at the gingival region permits contact of saliva with the cement used for fixing the tooth or crown in position which ultimately results in the attack of the cement by oral fluids, and can ultimately lead to dislodgement of the tooth.

It is an object of the present invention to provide for a more accurate manufacture and fitting of an artificial tooth construction.

According to the present invention a matrix for an artificial tooth construction is formed by electrolytically depositing a suitable metal onto a preformed model and thereafter an artificial tooth construction is built up on the matrix so formed Electroforming is not new in the dental field; it is however, a novel departure to produce a matrix by electrodeposition and to build up porcelain layers thereon.

The matrix may be formed from any suitable metal. However, gold is the most favoured metal, although platinum or other metals may also be employed. Alternatively, a composite metallic layer may be deposited electrolytically, for example a layer of gold alloy such as an alloy of gold with platinum, palladium, rhodium, silver, copper nickel, cobalt or indium may be deposited from an electrolyte containing the desired ions.

Yet again, separate metallic layers may be electrolytically deposited and subsequently converted into an alloy for example, by heat treatment. In particular gold may be thus alloyed for example with platinum, palladium, rhodium, silver, copper, nickel, cobalt or indium.

The method of the present invention may be applied in a variety of ways, for example, for the manufacture of tooth or cavity insertions, complete porcelain teeth, porcelain/metal composite teeth or crowns, all of which are included in the word "reconstruction" as hereinafter used. "Reconstruction" is used to refer to a porcelain-metal composite by itself apart from the article after it has been adhesively bonded in place as in or on a tooth.

The method of the present invention involves the production of an electroformed matrix, i.e. a matrix formed by electrodeposition of a metal in a preformed model. This method has significant advantages, particularly in that the electroformed matrix so produced is accurate and conforms substantially precisely to the model on which it is formed.

The preformed model would normally, although not exclusively, be produced from a plaster material commonly referred to as "artificial stone". In the case of a matrix formed from platinum, such as artificial stone model should be protected to prevent chemical attack of the model by the electrolyte which may be for example, platinic chloride solution.

The model may be protected from chemical attack for example, by means of an epoxy resin composition, e.g. an epichlorohydrin-bisphenol A condensation product.

The invention may be illustrated by reference to a variety of applications which for convenience are described by reference to constructions in gold and/or porcelain as follows, although it should be understood that other materials previously mentioned may be used:

Simple Inlay Construction

An impression of a tooth cavity is taken in a conventional manner and the surface of the impression metallised, for example with a metallic paint, to render it electrically conductive. The impression is thereafter placed in a bath of an appropriate electrolyte such as an aurocyanide complex solution, and a gold matrix electrodeposited on the surface of such impression. The matrix is thereafter removed from the impression material and porcelain is fused into the matrix, after which the gold is removed from the porcelain by dissolution with aqua regia.

The resulting porcelain inlay conforms exactly to the cavity in the tooth from which the impression was taken and may be cemented accurately into such cavity in the usual way.

Such embodiment is illustrated sequentially in the accompanying FIGS. 1a to 1h.

Full Porcelain Crown

An impression of the patient's tooth is taken in the usual way and a model of the tooth is formed from such impression in known manner. Such model is then metallised with metal paint and a gold matrix electrodeposited thereon as before. The matrix is then removed from the model and porcelain is built up on the matrix as previously. The matrix is again removed by dissolution in aqua regia, leaving a crown which accurately conforms to the patient's tooth and which may be cemented thereon as before. As an alternative, the gold matrix may be allowed to remain in the crown and the edges of the matrix may be burnished around the base of the tooth after fitting in order to provide an accurate fit and to exclude oral fluids from the cement employed for fixing of the crown into position.

In a further variation, a small vent hole may be provided in the matrix, for example, by locating a filament of nylon or other convenient material in the original model taken from the impression so that during electroforming, a small vent tube is formed in the matrix around which porcelain is built up in due course. The provision of such a vent assists in relieving pneumatic pressure which might otherwise build up during the cementing of the crown into position. Such vent may afterwards be plugged off or, alternatively, may be used to secure a small fixing screw to the patient's tooth to retain the crown even more securely in position. These embodiments are sequentially illustrated in FIGS. 2a to 2k.

Porcelain/metal bonded crowns

The production of composite porcelain/metal crowns also suffers from certain disadvantages, including discrepancies between the thermal performances of the metal and the porcelain, poor colour match of the metal and the porcelain especially at the gingival area of the tooth, and difficulties in obtaining an accurate fit in the patient's mouth.

In the construction of such composite crowns, a tooth model may be provided as hereinbefore described, and porcelain/metal, adapted for bonding firmly to the matrix is then cast and/or built up on such matrix with or without the provision of a vent. Again the bottom edge of the matrix may be extended beyond the cast metal and/or built up porcelain in order to provide a margin which afterwards may be burnished down to provide close fitting at the gingival area of the tooth. Such embodiment is illustrated in FIGS. 3a to 3c.

The methods hereinbefore described refer to the production of models by means of a male molding procedure. However, a female molding procedure may equally be well employed, the gold matrix being deposited on the internal surface of the mold and subsequently removed therefrom.

By means of combined male and female procedure it is possible to produce a particular form of crown which enables the poor colouring effects of porcelain bonded over metal at the gingival area to be avoided. According to such method respective corresponding gold matrices are produced by electroforming by male and female procedures. Again vents may or may not be included as desired. On the male produced matrix, a metal core is cast for example, by means of the "lost wax" method whereby, metal is formed more thickly on one side of the matrix and less thickly on the other (forward facing) side of the tooth matrix. A portion is then removed from the gingival margin of the forwardly facing part of the matrix and the female-formed matrix is fitted within the remaining portion of the male-formed matrix. Porcelain is thereafter built up over the forward surface of the tooth. In this way the crown at the forward gingival area is formed entirely of porcelain on a gold matrix, which avoids the discolouring effect which is noted when porcelain is built up on a metal substrate due to the translucent nature of the porcelain. As previously the margin of the matrix may be extended for burnishing into a close fitting around the base of the tooth. Such procedure is illustrated in FIGS. 4a to 4m. Preferably, in order to assist the separation of the matrices (FIG. 4f), following the treatment, a flash coating of electrolytically deposited platinum may be applied to one or both matrices. This prevents fusion of the matrices which would be course prevent their separation.

A further embodiment of the present invention permits the formation of relatively soft metal margins on hard cast metal teeth. The use of certain alloys for casting teeth or tooth surfaces, for example, gold alloy, cobalt/chromium or nickel/chromium alloys does not permit close marginal burnishing because of the hard nature of the alloys required by the duties to be performed by the teeth.

In accordance with the invention a cast tooth, as hereinbefore described, may be bevelled at the gingival areas and the casting coated with a non-conductive material to prevent the deposition of metal thereon during an electroplating process. The marginal areas of the casting are left uncoated and the construction is then electroplated with gold as before, leading to deposition of pure gold to form a margin which may be burnished into a close fitting in a patient's mouth as already described. This procedure may be employed not only for the production of new crowns, but also to the repair if necessary of existing crowns. Such procedure is illustrated in FIGS. 5a to 5e.

According to the invention a method is also provided for the electroplating of female molds to build up the deposit on the interior surface of such mold. In a normal method the interior of a mold is filled with appropriate electrolyte and an anode immersed therein to permit electrolysis to proceed. This however, does tend to lead to an uneven deposition of metal. According to the present method, a hollow anode is employed, the electrolyte being circulated through the metal via such anode. The electrolyte may be injected through the anode into a mold, or preferably introduced into the mold and extracted via the anode, this latter method avoiding erosion of metal deposited on the interior mold surfaces, as illustrated in FIGS. 6a and 6b.

In an extension of the prevent invention there is envisaged an improvement in the method of fixing metal based artificial tooth inlays or crowns into a patient's mouth, i.e. inlays or crowns formed wholly from metal or from porcelain laid on a metallic matrix as hereinbefore described.

Crowns or inlays or normally cemented into position but conventional cements employed for the purpose do not always provide a sufficiently effective bond between the crown or inlay and the tooth to which it is to be affixed. Cements customarily employed for this purpose, such as zinc phosphate cements, zinc oxide eugenol cements or even the recently developed polyacrylic acid based cements may proviee a mechanical bond between the cement and the metal (e.g. gold) base of perhaps 2-3 Newtons per square millimeter, which is not really adequate to withstand the forces to which the tooth may be subjected.

It has been found that if an artificial inlay or crown of metal or incorporating a metal base is treated to deposit a coating of a different metal on the surface of the metal or metal base, such coating can substantially improve the ability of that surface to form an effective bond with other materials.

The different metal may conveniently be deposited electrolytically or by vacuum deposition, preferably as a coating not exceeding 1 micron in thickness.

Such a procedure has two main applications. Firstly it permits improved bonding between the metal base of a crown or inlay and chelating cements which have been relatively recently developed for use in restorative dentistry.

The term chelating cements means those cements which appear to have the ability to form chemical bonds with the calcium ions in natural tooth enamel. Until the development of these cements, which are at present based on polyacrylic acid, it has been extremely difficult to bond crowns or inlays to natural teeth because of the inability of the cement to form strong, and particularly chemical, bonds with natural tooth enamel. Modern chelating cements therefore have significantly improved the fixation of crowns and inlays because of their ability to bond effectively, and apparently chemically, with the tooth enamel.

Examples of such chelating cements which are available commercially include those known as "Durelon" and "PCA" marketed respectively by the E.S.P.E. company of Germany and S.S. White & Co. of the U.S.A.

However, such chelating cements, although they form extremely strong bonds with tooth enamel, do not form correspondingly strong bonds with the passive material of the crowns and inlays themselves. The method permits an extremely strong bond to be formed between such chelating cements and the metal or metal base of artificial tooth crowns and inlays, thereby assisting in the full realisation of the potential of such cements.

Suitable metals include iron, tin, zinc, copper, nickel, chromium, cobalt, vandium, platinum and palladium. The preferred metal will depend upon the precise application involved.

The metal coating as stated is preferably deposited by known electrolytic or vacuum techniques to give a fine surface coating on the metal base of the artificial tooth, crown or inlay.

Before chelating cement (as hereinbefore described) is applied to the metal surface, the surface is desirably treated with a dilute mineral acid, for example, hydrochloric or nitric acid to create suitable ionic conditions on the surface, to promote interaction between the surface and the cement. The polyacrylic acid component of the cement is then applied to the pretreated surface, and the mixed cement is applied thereto.

The method, as stated, permits bonds of greatly increased strength to be obtained and, for example, bond strengths in tensile testing of 18 Newtons per square millimetre and higher can be achieved.

Secondly, the method permits improved bonding between the metal base of a crown or inlay and the ceramic material built up thereon. This improvement is achieved apparently, not through a mechanism similar to that described in connection with the chelating cements referred to above, but because of an improved fluxing during the firing procedure for building up the ceramic on the base, although the precise mechanism is not fully understood. In this embodiment acid pretreatment of the metal surface is not necessary.

For this technique, the same metals may be similarly used, and in addition indium may also be employed. However, for aesthetic reasons, certain metals such as copper may be less satisfactory because of their tendency to cause discoloration of the tooth, although the bonding quality of the surface is not impaired.

While the method of the invention is particularly applicable to treating gold bases of the type usually employed in restorative dentistry, it is also applicable to other alloys, such as nichrome which are on occasions used. The method of the invention does moreover permit the use of gold alloys of non-specialised type to be bonded to ceramic material which has not been satisfactory, hitherto requiring the use of special alloys containing expensive trace elements.

Although the method has been described with particular reference to the cementing of artificial tooth inlays or crowns, the method is also applicable to the fixing of endosseous implants, as effective bonding can be achieved with the bone structures as well as tooth enamel.

The method is illustrated to particular reference to the following example.

10 brass tensile specimens were gold plated to duplicate a crown base surface. The gold surfaces were then nickel plated in an electrolytic bath for 30 seconds to give a "flash" nickel deposit approximately 0.4 millligrammes thick.

A 10% solution of nitric acid was thinly and lightly brushed on to the acid treated surface.

"Duralon" carboxylate cement was mixed for 30 seconds and then spaced on the pretreated surface, which were then stuck together in pairs and allowed to stand for 5 minutes under a pressure of 10 kilogrames per centimeter. The paired samples were placed in a humidor for 24 hours under 100% humidity at 33% centigrade. The samples were then tensile tested and the bond strengths were found to be 18 Newtons per square millimetre with a standard deviation of 3.

I claim:
1. A method of making a porcelain and metal tooth reconstruction, the metal being positioned with respect to the porcelain so as to be adapted to serve as a surface of contact with adhesive when the reconstruction is adhesively attached to a tooth, the method comprising:
   forming a model of the reconstruction,
   applying a conductive coating on said model,
   electrolytically depositing a layer of a first metal selected from the group consisting of gold, platinum, palladium, rhodium and alloys thereof on said conductive coating,
   removing said model from said layer of said first metal and forming a porcelain reconstruction having a desired shape against a surface of said metal, and then
   electrolytically depositing on said layer of said first metal on a side opposite said porcelain, a second metal different from said first and selected from the group consisting of iron, tin, zinc, nickel, chromium, cobalt, vanadium, platinum and palladium.

2. The method of claim 1 wherein said reconstruction is adapted to be used as an inlay and said metal forms a jacket about a portion of said porcelain.

3. The method of claim 1 wherein said reconstruction is adapted to be used as a crown and said metal is disposed so as to form a socket for said crown.

4. A method according to claim 1, wherein a vent is formed in the metal in order to assist the relief of pneumatic pressure when the reconstruction is secured in position in the patient's mouth.

5. A method according to claim 1, wherein the model is produced from a plaster material which is then protected, for example by coating with an epoxy resin, prior to the electrolytic deposition of metal thereon.

* * * * *